United States Patent [19]

Herrmann et al.

[11] Patent Number: 4,506,071

[45] Date of Patent: Mar. 19, 1985

[54] PROCESS FOR PREPARING MICROCRYSTALLINE ISOXICAM

[75] Inventors: Wolfgang Herrmann, Merzhausen; Uwe Gebhardt, Waldkirch, both of Fed. Rep. of Germany

[73] Assignee: Warner-Lambert Company, Morris Plains, N.J.

[21] Appl. No.: 588,420

[22] Filed: Mar. 12, 1984

[30] Foreign Application Priority Data

Mar. 26, 1983 [DE] Fed. Rep. of Germany ....... 3311165

[51] Int. Cl.³ .................. C07D 413/12; C07D 417/12
[52] U.S. Cl. ...................................................... 544/49
[58] Field of Search ........................................... 544/49

[56] References Cited

U.S. PATENT DOCUMENTS

| 3,821,211 | 6/1974 | Sircar et al. | 544/49 |
| 3,957,772 | 5/1976 | Fabian et al. | 544/49 |
| 3,960,856 | 6/1976 | Genzer et al. | 544/49 |
| 3,987,038 | 10/1976 | Fabian et al. | 544/49 |
| 4,018,762 | 4/1977 | Fabian et al. | 544/49 |
| 4,024,136 | 5/1977 | Genzer et al. | 544/49 |
| 4,100,347 | 7/1978 | Hammen | 544/49 |

Primary Examiner—John M. Ford
Attorney, Agent, or Firm—Ronald A. Daignault

[57] ABSTRACT

A new process for the preparation of microcrystalline isoxicam having a particle size of about 1-30 μm which comprises dissolving isoxicam in a mixture consisting of a solvent miscible with water and of an aqueous base where the resulting basic solution is neutralized with dilute acid to a pH of 4-6 with vigorous agitation precipitating the microcrystalline product is herein described.

3 Claims, No Drawings

PROCESS FOR PREPARING MICROCRYSTALLINE ISOXICAM

BACKGROUND OF THE INVENTION

Isoxicam is an active material of the 1,2-benzothiazine-1,1-dioxide group known from U.S. Pat. No. 3,787,324. It is used as a non-steroidal anti-inflammatory agent.

Since isoxicam is relatively poorly water-soluble, there arise difficulties with regard to the bioavailability with oral administration and, by suitable means, care must be taken that a sufficient resorption takes place which, above all, is independent of external conditions and of the patient and is uniform.

As a rule, in the case of poorly resorbed materials, the attempt is made either mechanically to comminute to a usable particle size the relatively large grained crystals obtained in the production or purification process of the active material or one so selects the crystallization conditions that, from the very beginning, crystals of the desired size are obtained.

In the case of mechanical comminution, for example micronization by means of jet mills, it is practically not possible to achieve a uniform particle size since the milling procedure produces fragments of the original crystals in the most varied sizes. Furthermore, jet mills are expensive not only in purchasing them but also in operation and achieve only a relatively small substance output per unit time.

The recrystallization of poorly soluble substances also leads, even when usable conditions with regard to solvents and crystallization conditions can be determined, to high substance losses because a complete recovery from the mother liquor is only possible with high costs. It is also difficult to achieve uniform crystal size.

In the case of precipitation processes which can give very finely divided particles, in most cases the precipitate is obtained amorphous or so finely crystalline that the further handling (centrifuging, filtration, drying, etc) is made extremely difficult.

Surprisingly, it has now been found that isoxicam is obtained crystalline in readily workable and outstandingly resorbable form.

SUMMARY AND DETAILED DESCRIPTION

Accordingly, the present invention relates to a process for preparing microcrystalline isoxicam having a particle size of about 1–30 μm (90% between 2 and 25 μm), which comprises dissolving isoxicam in a mixture consisting of a solvent miscible with water and of an aqueous base, where the resulting solution is at a pH of 8–9; adding dilute acid to a pH value of 4–6 with vigorous agitation; separating the deposited precipitate from the mother liquor; washing with water, and drying the product to constant weight at 50°–60° C.

As examples of suitable solvents, lower alcohols, tetrahydrofuran, dimethylformamide, dioxane, and especially acetone may be used.

As base, ammonia solution has proved to be especially useful. However, it is also possible to use dilute, preferably one normal aqueous potassium or sodium hydroxide solution.

Isoxicam may be obtained in crude or purified form as described in U.S. Pat. No. 3,787,324 or according to processes described in U.S. Pat. Nos.: 3,821,211, Re 29,836, 3,957,772, 3,960,856, 3,987,038, 4,018,762 and 4,024,136.

If crude isoxicam is used as starting material for the preparation of the product according to the invention, then filtration may be necessary before the precipitation, i.e., addition of the acid, after previous treatment with active charcoal since an especially pure product is thereby achieved.

In addition to organic acids, such as acetic acid or propionic acid, as precipitation agents, mineral acids, such as hydrochloric or sulphuric acid in about one normal dilution are also suitable.

It is to be regarded as very surprising that in carrying out the precipitation according to the invention, isoxicam is obtained in a microcrystalline form which, in addition, is characterized by a very uniform particle size distribution.

The substance is present as a white, floury powder in a particle size between 1 and 30 μm (2.0 μm<90%<25 μm) and thus corresponds approximately to the substantially more laboriously produced isoxicam which has been micronized by means of jet mills (1 μm<90%<15 μm). The particle size analyses were carried out with a Coulter counter.

It is surprising that the product according to the invention, in spite of the fine-grained structure, does not tend to stick or cake.

Investigations have shown that an important reason for this is because water is exclusively used for the washings, e.g. on a centrifuge. When organic solvents are used, one obtains, even with dilution with water, hard agglomerates which can scarcely be comminuted.

If, however, after the centrifuging of the mother liquor, one only washes with water, one obtains a loose powder which, even in the case of sieving, is completely divided up.

Unexpectedly, independently of the particle size, the solubility properties of the microcrystalline active material are substantially better than those of the micronized active material.

Microcrystalline isoxicam dissolves in a buffer solution of pH 9 at 37° C. twice as quickly as isoxicam of normal particle size (10–200 μm; nonmicronized) and in about 25% shorter time than micronized isoxicam.

A similar effect is shown in the case of tablets and gelatine capsules produced with various isoxicam qualities: the forms of administration with micronized active material give experimentally (Sartorius dissolution model) an approximately 50% slower dissolution than the forms produced with microcrystalline active material.

Since the average particle size of the microcrystalline isoxicam is somewhat higher than that of the micronized active material, a quicker dissolving of the micronized isoxicam was to have been expected.

Studies of the bioavailability also showed a significant superiority of the microcrystalline isoxicam according to the invention. Tablets and capsules with microcrystalline active material gave, in the case of the same galenical formulation, an approximately 100% higher relative bioavailability than tablets and capsules with micronized active material; in the case of suppositories, an approximately 23% better bioavailability was found when microcrystalline isoxicam had been used instead of micronized isoxicam for their production.

Thus, the process according to the invention leads, in a simple manner, to an outstandingly resorbable active material which, from every point of view, can be handled without problems.

The following Example serves for the more detailed explanation of the invention:

EXAMPLE 1 kg of crude isoxicam is dissolved, with stirring, at room temperature in a mixture of 8 l acetone and 8 l 0.5N aqueous ammonia solution. A pH value of about 8 is obtained. Subsequently, the solution is stirred with 0.3 kg active charcoal for 15 minutes and is then filtered. One allows 4.8 l 1N acetic acid to run into the filtrate with good stirring, whereby a pH of 5-6 results, then stirs briefly and separates off the precipitate by centrifuging of the mother liquor. The crystallizate is washed three times with, in each case, 2 l demineralized water and subsequently dried in a circulating air drying cabinet at 55°-60° C. up to constant weight.

The dry substance is passed through a sieve with 0.5 mm mesh size (35 mesh), whereby loose lumps possibly present automatically break up.

Yield:
860 g=86% of theory
Purity according to TLC and HPLC>99%
Particle size between 1 and 30 μm The precipitation can also be carried out with the use of mineral acids and also, in the reverse manner, in that one allows the basic solution of isoxicam to run into the aqueous acid provided.

The mixture of the solutions may also be carried out in a continuous process.

As starting product, there can also be used pure isoxicam. In this case, a treatment of the solution with charcoal is not necessary and the yield lies at about 95%.

We claim:

1. A process for the preparation of a microcrystalline form of isoxicam having a particle size of about 1-30 μm (90% between 2 and 25 μm) comprising dissolving isoxicam in a mixture consisting of a water-miscible solvent and an aqueous base where the resulting solution is at a pH of about 8-9; adding dilute acid to a pH value of 4-6 with vigorous agitation; separating the deposited precipitate separated from the mother liquor; washing with water and drying the product at 50°-60° C.

2. A process according to claim 1, wherein the water-miscible solvent is acetone and the aqueous base is aqueous ammonia.

3. A process according to claim 1 or 2, wherein the solution is filtered before addition of the acid.

* * * * *